US010292622B2

United States Patent
Cuba Gyllensten et al.

(10) Patent No.: US 10,292,622 B2
(45) Date of Patent: May 21, 2019

(54) BIOIMPEDANCE SPECTROGRAPHY SYSTEM AND METHOD

(71) Applicant: KONINKLIJKE PHILIPS N.V., Eindhoven (NL)

(72) Inventors: Illapha Gustav Lars Cuba Gyllensten, Stockholm (SE); Alberto Giovanni Bonomi, Eindhoven (NL); Jarno Mikael Riistama, Waalre (NL); Jennifer Caffarel, Eindhoven (NL); Harald Reiter, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 381 days.

(21) Appl. No.: 14/373,927

(22) PCT Filed: Feb. 7, 2013

(86) PCT No.: PCT/IB2013/051014
§ 371 (c)(1),
(2) Date: Jul. 23, 2014

(87) PCT Pub. No.: WO2013/121327
PCT Pub. Date: Aug. 22, 2013

(65) Prior Publication Data
US 2014/0358021 A1 Dec. 4, 2014

Related U.S. Application Data

(60) Provisional application No. 61/598,936, filed on Feb. 15, 2012.

(51) Int. Cl.
*A61B 5/08* (2006.01)
*A61B 5/00* (2006.01)
*A61B 5/053* (2006.01)

(52) U.S. Cl.
CPC .......... *A61B 5/0816* (2013.01); *A61B 5/0535* (2013.01); *A61B 5/6823* (2013.01); *A61B 5/6831* (2013.01); *A61B 5/7289* (2013.01)

(58) Field of Classification Search
None
See application file for complete search history.

(56) References Cited

U.S. PATENT DOCUMENTS 5,746,214 A * 5/1998 Brown ................ A61B 5/0536
600/484
7,122,010 B2 10/2006 Bohm et al.
(Continued)

FOREIGN PATENT DOCUMENTS

| | | |
|---|---|---|
| JP | 2005118148 A | 5/2005 |
| KR | 20040075681 A | 8/2004 |
| KR | 2006036965 A | 5/2006 |
| WO | 0033733 A1 | 6/2000 |
| WO | 20080029316 A2 | 3/2008 |
| WO | 2012008251 A1 | 1/2012 |

OTHER PUBLICATIONS

Ernst, et al. Impedance pneumography: Noise as signal in impedance cardiography, Psychophysiology, 36 (1999), 333-338.*
(Continued)

*Primary Examiner* — Tiffany Weston
*Assistant Examiner* — Jay B Shah

(57) ABSTRACT

A device and method for bioimpedance spectrography corrects for breathing artifacts. A breathing signal is used in conjunction with an impedance signal to adjust for a point in time within a respiratory cycle of a user at which the measurements are made. The correction allows the device to characterize tissue parameters accurately with fewer measurement points.

18 Claims, 3 Drawing Sheets

(56) References Cited

U.S. PATENT DOCUMENTS

| | | |
|---|---|---|
| 7,869,866 B2 | 1/2011 | Loriga et al. |
| 7,970,462 B2 | 6/2011 | Lefkov et al. |
| 8,032,212 B2 | 10/2011 | Bornzin et al. |
| 8,150,507 B2 | 4/2012 | Hamaguchi et al. |
| 8,781,551 B2 | 7/2014 | Chetham |
| 8,868,175 B2 | 10/2014 | Arad |
| 2004/0006279 A1 | 1/2004 | Arad |
| 2004/0073130 A1 | 4/2004 | Bohm et al. |
| 2006/0241513 A1 | 10/2006 | Hatlestad et al. |
| 2006/0247543 A1 | 11/2006 | Cornish et al. |
| 2007/0142733 A1 | 6/2007 | Hatlestad et al. |
| 2009/0143663 A1* | 6/2009 | Chetham .............. A61B 5/053 600/372 |
| 2010/0130885 A1* | 5/2010 | Hamaguchi .......... A61B 5/0537 600/547 |
| 2010/0198100 A1 | 8/2010 | Oku et al. |
| 2010/0204601 A1 | 8/2010 | Masuo |
| 2011/0066041 A1* | 3/2011 | Pandia ................. A61B 5/113 600/484 |
| 2013/0090543 A1 | 4/2013 | Murakawa et al. |
| 2014/0358021 A1 | 12/2014 | Gyllensten et al. |
| 2015/0119947 A1 | 4/2015 | Feldman et al. |

OTHER PUBLICATIONS

Cole et al, "Dispersion and Absorption in Dielectrics", Journal of Chemical Physics, vol. 9, Apr. 1941, pp. 341-351.

Brown et al, "Neonatal Lungs: Maturational Changes in Lung Resistivity Spectra", Medical & Biological Engineering & Computing, vol. 40, 2002, pp. 506-511.

Maier et al, "Abstract 2396: Device-Based Heart Failure Management: Multi-Frequency Impedance Measurements to Optimize Intrathoracic Fluid Monitoring", Circulation, 2008, 1 Page.

Mazeika et al, "Respiratory Inductance Plethysmography an Introduction", Pro-Tech Services, Inc. 2007, pp. 1-13.

Lagarias et al, "Convergence Properties of the Nelder-Mead Simplex Method in Low Dimensions", Society for Industrial and Applied Mathematics, Siam J. Optim., vol. 9, No. 1, 1998, pp. 112-147.

Ernst et al. Impedance pneumography: Noise as signal in impedance cardiography, Psychophysiology, 46 (1999), 333a 338.

Cole, K.S. et al., "Dispersion and Absorption in dielectrics", J. Chem. Phys., vol. 9, pp. 341-350, 1941.

Ernst, J.M. et al., "Impedance pneumography: Noise as signal in impedance cardiography". Psychophysiology, 36 (1999), 333a 338.

\* cited by examiner

BIOIMPEDANCE SPECTROGRAPHY SYSTEM AND METHOD

CROSS-REFERENCE TO PRIOR APPLICATIONS

This application is the U.S. National Phase application under 35 U.S.C. § 371 of International Application No. PCT/IB2013/051014, filed on Feb. 7, 2013, which claims the benefit of U.S. Provisional Patent Application No. 61/598,936, filed on Feb. 15, 2012. These applications are hereby incorporated by reference herein.

TECHNICAL FIELD OF THE INVENTION

This invention relates to a bioimpedance spectrography system and method, and in particular relates to a system and method which compensates for breathing artefacts.

BACKGROUND TO THE INVENTION

A common symptom in heart failure patients with low left ventricle ejection fraction is the build up of fluids in the lungs. As the heart cannot manage to pump away enough of the blood, fluids build up and cause diminished respiratory capacity and increased strain on the heart.

Commercial systems that monitor fluid build up currently measure impedance at a set frequency. However, to improve the assessment of fluid build up a more complete characterisation of the tissue using several frequencies has been suggested.

It is well known that the Cole-Cole model is a good approximation of human tissue properties in the frequency band between 10-1000 kHz and this model has seen extensive use in body composition estimation algorithms, and some applications in lung tissue characterisation and cardiac assessment (for example as disclosed in US 2006/0247543).

To research the possibilities of including such measurements in a home monitoring solution Philips has developed a wearable bioimpedance device which cycles through a set of frequencies and measures the corresponding impedance.

However, bioimpedance is also affected by various other influences, for example how the tissue is distributed between the measurement points, effects of tissue compression, blood perfusion, air inflow etc. These changes are also picked up during the measurement. In fact, recording impedance to measure some of these signals is well-known in the fields of impedance cardiography and impedance pneumography.

A device that captures impedance values at several frequencies will inevitably capture some of these values at different stages of the respiratory cycle. Current methods solve this problem by averaging over several measurement cycles (also referred to as "sweeps"). However this leads to a long measurement time during which the subject is required to be still. The absolute time depends on the speed of the electronics and accepted error levels of the tissue parameters.

SUMMARY OF THE INVENTION

The invention is directed to the problem of breathing distortions reducing the accuracy of a multiple frequency bioimpedance spectrum.

In one aspect, the invention provides a bioimpedance spectrography system comprising:
a bioimpedance measurement system comprising:
a current source for applying an ac current to the body tissue;
a reading arrangement for reading a voltage from the body tissue;
a controller for varying the frequency of the ac current applied to the body tissue;
a processor for deriving a frequency-dependent impedance function from the applied current values and the read voltages; and
a breathing monitor for monitoring or deriving a breathing pattern of the user, wherein the processor is further for processing a tissue characterisation function, the monitored or derived breathing pattern and the frequency-dependent impedance function in order to derive tissue parameters.

The invention provides a method and system in which a breathing signal is captured and is used to adjust for the changing geometry during respiration on the tissue characterisation function, and thereby the tissue parameter estimation. In this way, bioimpedance spectrography is corrected for breathing artefacts. This is achieved by using a breathing signal in conjunction with the impedance signal to make adjustments to take account of the point in time in the respiratory cycle at which the measurements are made. The correction allows the device to characterize tissue parameters accurately with fewer measurement points.

The correction involves making adjustments to take account of when in the respiratory cycle the impedance values are recorded, using the relation that impedance is positively correlated with respiration. Thus, at maximum inhalation the impedance is at a peak and during maximum exhalation the impedance is at a minimum. This allows for a shorter period to be used to extract accurate parameters.

The tissue characterisation function is effectively normalised at each frequency to take account of the effect of breathing on the impedance measurements at each frequency.

The means for monitoring or deriving a breathing pattern can comprise a breathing sensor which is separate to the bioimpedance measurement system, for example an inductive belt.

Alternatively, the means for monitoring or deriving a breathing pattern can comprises a processor for analysing the frequency-dependent impedance function to extract the breathing pattern signal. In this way, impedance signals are used to derive the breathing pattern, and thus enable a modified tissue characterisation function to be derived. For example, the breathing monitor signal can be obtained for a set of frequencies based on the instantaneous impedance signal at each frequency and the average impedance signal at the frequency. In this way, deviations from an average impedance signal (at a particular frequency) are attributed to the breathing pattern.

The processor can be adapted to map the derived frequency-dependent impedance function to the corrected tissue characterisation function to derive tissue characterisation parameters. By using the corrected tissue characterisation function, the tissue characterisation parameters can be more accurate and/or they can be derived from a smaller data set.

In another aspect, the invention provides a bioimpedance spectrography method comprising:
applying an ac current to body tissue;
reading a voltage from the body tissue;
varying the frequency of the ac current applied to the body tissue;

deriving a frequency-dependent impedance function from the applied current values and the read voltages;

monitoring or deriving a breathing pattern of the user, processing a tissue characterisation function, the monitored or derived breathing pattern and the frequency-dependent impedance function to derive tissue parameters.

BRIEF DESCRIPTION OF THE DRAWINGS

Examples of the invention will now be described in detail with reference to the accompanying drawings, in which.

DETAILED DESCRIPTION OF PREFERRED EMBODIMENTS

The invention provides a bioimpedance spectrography system (which can be of conventional type) in combination with a means for capturing the breathing signal. A breathing sensor can be used, such as a respiratory belt (inductive or using a strain sensor), a pneumograph or indeed the bioimpedance monitor itself after some signal processing is used to extract the breathing signal. The impedance and breathing signals are combined to reduce the time needed for measurement of tissue parameters.

Figure 1:
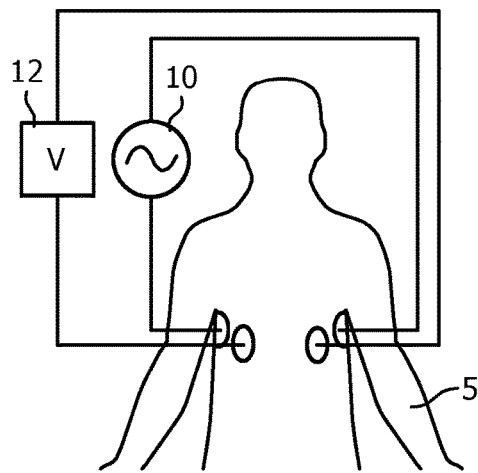
FIG. 1 shows a known bioimpedance monitoring system and which can be employed in the method and system of the invention.

FIG. 1 shows a known tetrapolar placement of electrodes on the thorax of a subject 5, and which can be used to capture the raw bioimpedance measurements (i.e. before the additional signal processing provided by the invention) within the system and method of the invention.

A set of electrodes is arranged in groups so that they are in electric contact with the subject's thorax. The electrodes are then connected to a device 10 which generates a sinusoidal electric signal which is provided across two of the electrodes while simultaneously recording the observed voltage drop between the other electrodes using a voltage meter 12. A tetrapolar arrangement is a standard arrangement in which two electrodes are on either side of a subject's thorax. One pair of electrodes on opposite sides of the thorax is used to inject a current through the chest while the voltage drop between the other pair of electrodes (adjacent to the electrodes injecting current) is recorded.

The voltage and current values are recorded for a period of time after which the frequency of the sinusoidal current is changed. This process is then iterated over a set of frequencies. Impedance is then calculated from the complex voltage and current according to Ohms law:

$$Z(t) = \text{Voltage}(t)/\text{Current}(t)$$

Different electrode arrangements can be used, and various frequency step sizes are possible, for example stepping in frequency steps of 10 kHz from 10 kHz to 1 MHz. The frequency steps can be variable, starting small and increasing in step size for larger frequencies.

The basic bioimpedance signal capture is not altered by the invention.

Figure 2:
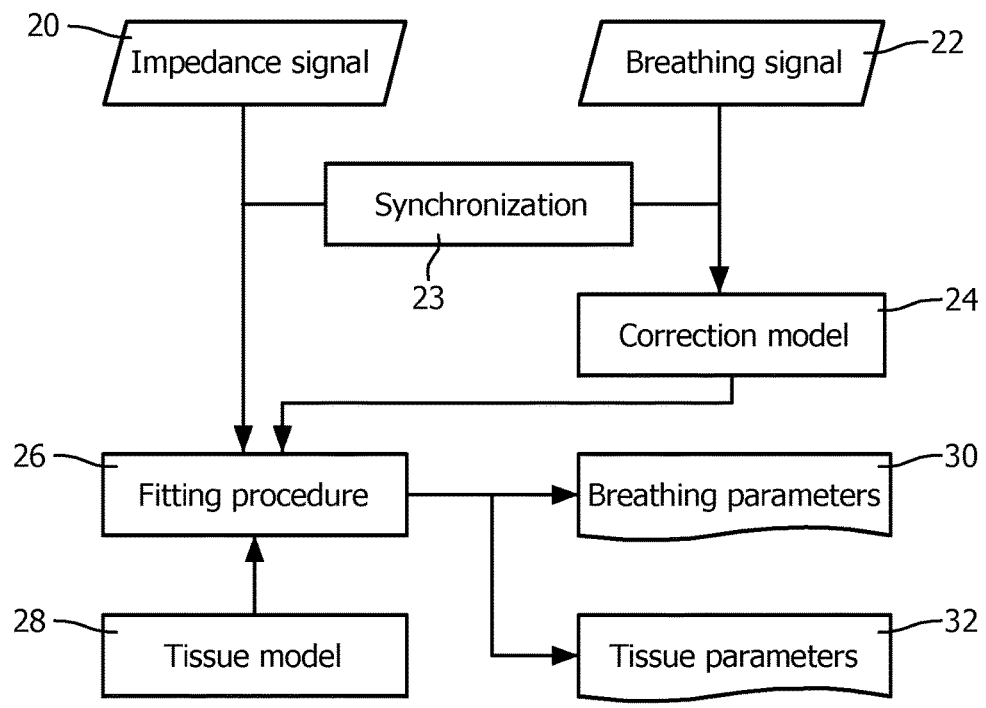
FIG. 2 is a flow chart used to explain the method of the invention.

In accordance with the invention, a breathing signal is extracted from the subject during this period and synchronized with the output from the impedance measurements. This process is shown in FIG. 2.

The process of capturing the breathing signal and combining it with a tissue model can be realized using different approaches, all within the general flowchart shown. The general process in FIG. 2 comprises obtaining an impedance signal by conventional means in step 20 and obtaining a breathing signal in step 22.

A synchronisation step (step 23) is optional, and can be used to resample the breathing data if has been collected at a different sampling rate, so that it matches the sampling rate of the bioimpedance signal.

A correction model is derived from the breathing signal (correction step 24), to be used for correcting an impedance-based tissue model. A fitting procedure in step 26 combines the tissue model shown by block 28 and the correction model 24, and using the impedance measurements, the fitting procedure outputs breathing parameters 30 and tissue parameters 32. The breathing parameters are not in fact needed as output, and the aim of the system is to generate the tissue parameters 32 in an accurate and time efficient manner.

Two detailed variations are discussed below.

In a first approach, the breathing signal is captured by an inductive breathing belt and then combined with the bioimpedance measurement as a normalized multiplicative factor.

In a second approach, the breathing signal is extracted from the impedance monitor and then combined with the tissue model as an additive factor. The conceptually important steps are that:

(i) A signal indicating chest expansionbreathing is captured simultaneously with the impedance measurements.

(ii) The breathing signal is combined with the tissue model in such a way that the impedance values captured during maximum inhalation are adjusted downward and impedance values captured during maximum exhalation are adjusted upward. Equivalently, the tissue model can be adjusted upwardly during maximum inhalation and downwardly during maximum exhalation. In both cases, it can be considered that a corrected tissue characterisation model is derived—either by including modification to the measured impedance values or by including modification to the model itself.

In the first approach using an inductive belt, this is fastened around the thorax over the electrodes, for example a device the zRIP from Respironics (Trade Mark). The voltage signal from the device is then normalized to have a mean of zero; a constant Bc is used for this normalization of the breathing belt signal:

$$\text{Mean}(B(t) - Bc) = 0$$

The breathing signal is B(t).

The tissue model in one example is the known Cole-Cole model described by the following equation, where $R_0$, $R_{inf}$, $\tau$, $\alpha$, are tissue parameters and j is the imaginary number.

$$Z = R_{inf} + (R_0 - R_{inf})/(1 + (j\omega\tau)^\alpha) \quad \text{(Cole-Cole model)}$$

The Cole-Cole model dates from 1941: "Dispersion and Absorption in dielectrics", J. Chem. Phys., 9 pp. 341-351.

The parameters in the model relate to different dielectric properties of the tissue:

$R_0$ is the modelled resistance of the tissue for a hypothetical DC current. It could therefore be seen to represent the resistance of extracellular fluid (more fluid implies less resistance).

$R_{inf}$ is the modelled resistance to a current with infinitely high frequency, from this parameter it is possible to extract the resistance of fluids bound within capacitive membranes.

$1/\tau$ is the characteristic frequency which describes the capacitive properties of the membranes dividing the fluids.

$\omega$ is the period of the frequency at which the impedance is measured.

$\alpha$ is an emperical number in the range of 0 to 1.

However, other tissue characterisation functions which relate tissue parameters to impedance can be used, and the invention is not limited to any particular tissue characterisation function.

The correction module can be used to implement a multiplicative factor:

$$Z(t)=\text{TissueModel}(\omega,\text{parameters})*\text{BreathingFactor}(t,\text{parameters})$$

For the Cole-Cole model, the parameters of the tissue model are those in the equation above. The parameters of the breathing factor are set out below.

The model parameters of the tissue model function are those that characterise the tissue being examined.

To find the model parameters (and thereby enable the tissue parameters to be determined), the impedance is effectively modified by the distortion caused by breathing. A set of parameters for each frequency can be used to model the breathing factor:

$$\text{BreathingFactor}(t)=k(\omega)\cdot(B(t)-Bc)+1$$

$k(\omega)$ and Bc are the parameters of the breathing factor function, where k is a complex number with absolute value greater than zero.

This breathing factor function has a mean of 1 so that on average, when used as a multiplier, the impedance function is not modified. The frequency dependent parameter set $k(\omega)$ implements the frequency dependent nature of the breathing factor function.

The breathing factor function is frequency dependent. During inhalation resistance increases, however it does not do this in an entirely linear fashion. The frequency dependency of the parameter k can adjust for this balance.

For simplicity the full expression is shown below with a single parameter k (i.e. the frequency dependency is ignored) for the breathing signal:

$$Z(t)=(R_{inf}+(R_0-R_{inf})/(1+(j\omega\tau)^\alpha))\cdot(k\cdot(B(t)-Bc)+1) \quad \text{Eq. 1}$$

In a second variation, the breathing signal is extracted from the bioimpedance measurements directly. The well known dependence of impedance on breathing can be extracted for each frequency by dividing by or subtracting the mean real impedance values at each frequency (a mean while varying the time t):

$$B(t)=(Re(Z(t,\omega))-\text{Mean\_}t(Re(Z(t,\omega))))$$

This function is based on the instantaneous impedance signal at the frequency and the average impedance signal at the frequency. Thus, the deviation from the average impedance value is attributed to the effect breathing is having on the measurements.

A filter can then be applied to this signal to remove frequencies which do not correspond to the breathing rate for example by removing all frequencies except those between 0.1 to 0.8 Hz (covering the physiological ranges of breathing frequency). The resulting signal is then added to the tissue model, i.e. the Cole-Cole model for the example given.

$$Z(t)=(R_{inf}+(R_0-R_{inf})/(1+(j\omega\tau)^\alpha))+(k\cdot(B(t))) \quad \text{Eq. 2}$$

In this embodiment, the breathing correction is added to the impedance rather than multiplied by it.

Equations 1 and 2 provide a time-based impedance function, where at each time t, one frequency is measured. The function mapping takes all of the different-frequency measurements to look for the best parameter fit to them all.

In both these variations, the resulting tissue characterisation functionmodel, corrected to account for respiration (as described by Equations 1 and 2), is compared to the actual impedance values captured by the impedance spectrometer. The tissue parameters and breathing parameters are then chosen to best explain the measured values. Thus, the corrected tissue characterisation function is mapped onto the measured results, and the function parameters (which define the tissue parameters being measured) are optimised by fitting the function to the results.

This function fitting can be implemented using several methods, one of which is presented below.

First a guess of reasonable parameters values is chosen (for example $R_0=25$, $R_{inf}=15$, $\alpha=0.65$, $\tau=1.8\cdot10^{-6}$, $k=0.4$), then an error is defined, for example:

$$\text{Sum over all time}\{Re(Z\text{observed}(t))-Re(Z(t))\}^2$$

This is a sum of squares of the difference between the observed results and the results predicted by the corrected tissue characterisation model. A parameter set is found which minimises this error measure.

The error can be minimized by performing a Nelder-Mead simplex search. This is for example the standard matlab minimization algorithm. However, many other function fitting algorithms can be used.

Figure 3:
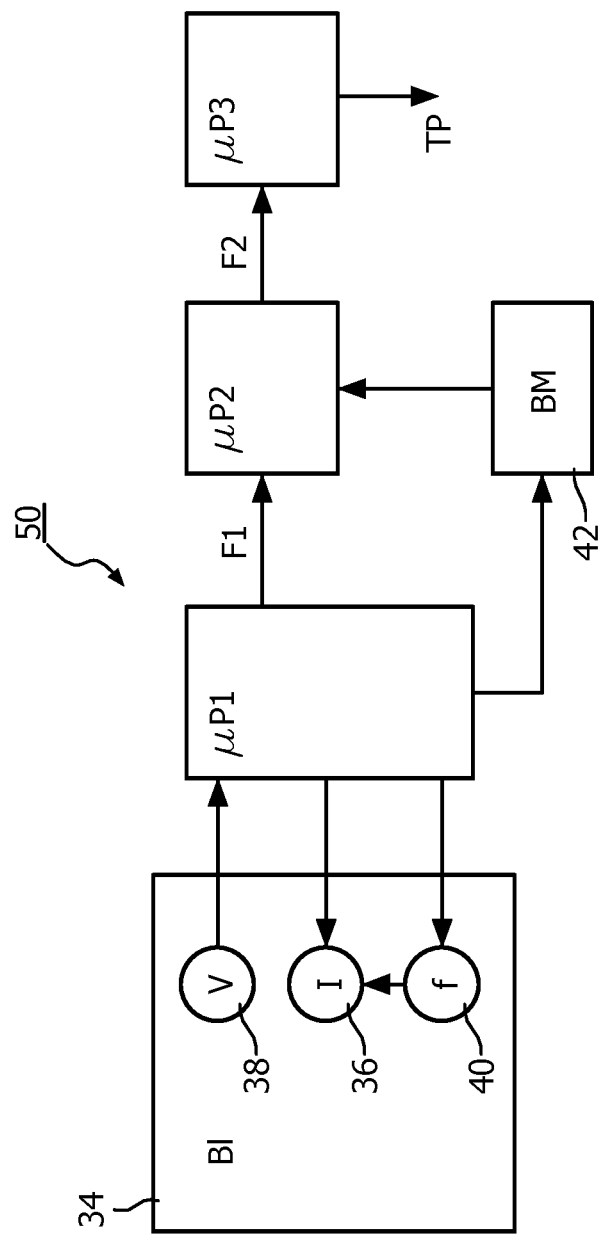
FIG. 3 shows the system of the invention.

The system 50 of the invention is shown in FIG. 3.

A known bioimpedance measurement system 34 has a current source 36 and contact pads for applying ac current to the user's body tissue and a voltage reading circuit 38 and contact pads for reading a voltage from the body tissue. The frequency of the ac current applied to the body tissue can be varied as shown by unit 40.

A processor can be considered to implement three separate functions, and these are shown as three processors µP1, µP2 and µP3. Of course, in practice all processing can be carried out by a single unit.

The first processor µP1 controls the bioimpedance measurement process, and provides a tissue characterisation function F1. This function F1 can be any known frequency-dependent characterisation function, which enables the impedance values (derived from the applied current values and the read voltages) to be mapped to tissue parameters forming the function F1.

A breathing pattern is monitored or derived by breathing monitor 42. As explained above, it may be a separate sensor device or it may be a processor function applied to the impedance data.

The second processor µP2 combines the tissue characterisation function F1 with the monitored or derived breathing pattern, and derives a corrected tissue characterisation function F2.

By function mapping, a third processor µP3 extracts the tissue parameters TP based on the corrected function F2.

Figure 4:
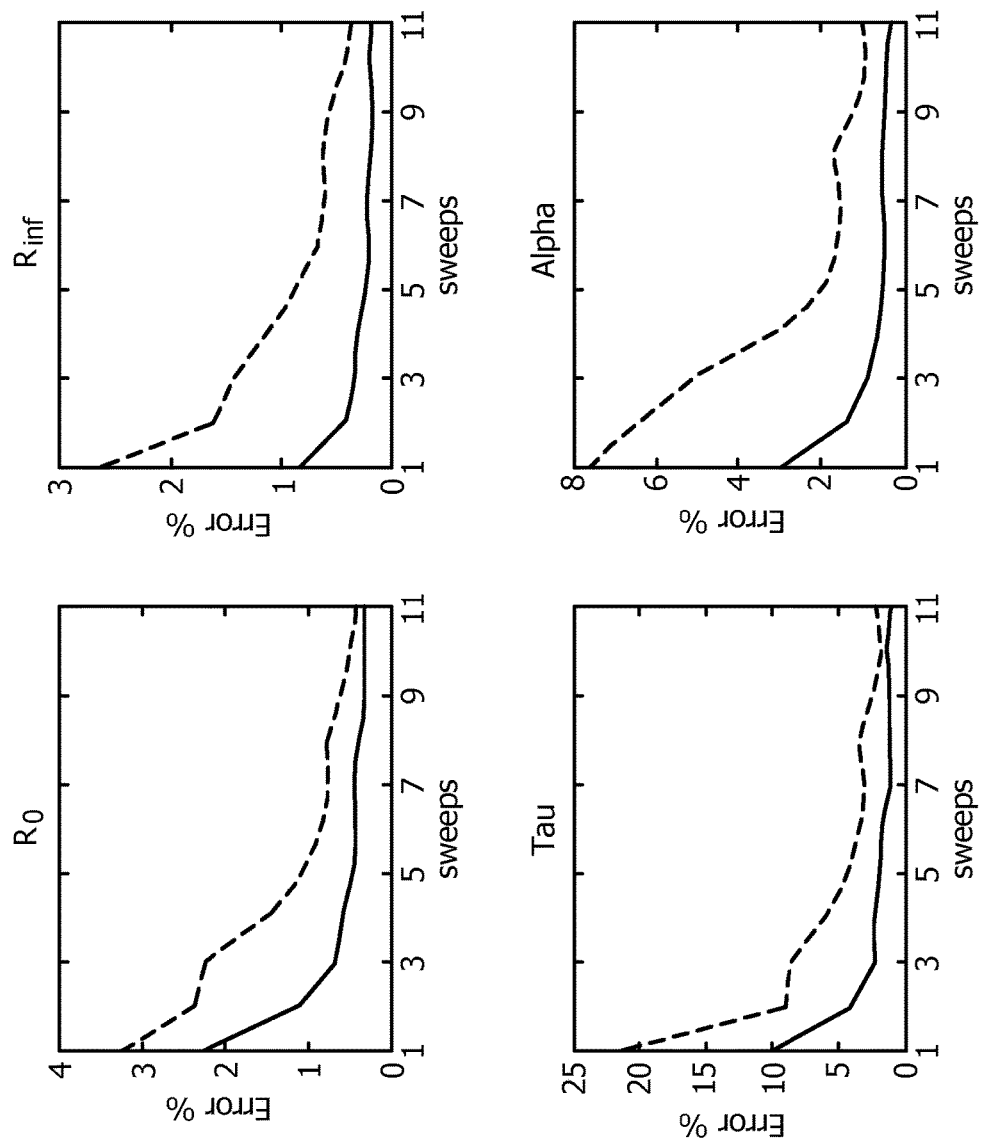
FIG. 4 shows the improvements obtained using the method and system of the invention.

The method and system of the invention allows for far fewer measurement cycles (sweeps) to be used to arrive at accurate tissue parameters, as shown in FIG. 4.

FIG. 4 shows median relative errors of estimated parameters for different numbers of measurement cycles (sweeps).

The top left graph shows the resistance $R_0$, the top right graph shows the infinite frequency resistance $R_{inf}$, the bottom left graph shows the tau value ($\tau$) and the bottom right graph shows the alpha value.

The relative error is calculated as the percentage difference of the estimated parameter value and the calculated parameter value using 84 sweeps.

In one example, each sweep can be around 3 seconds long. In each sweep, the full set of frequency measurements is obtained. Thus, each sweep gives a series of impedance measurements at different frequencies and different times. Because the sweeps are taken at different times, impedance values are sampled at different times in the breathing cycle. An individual impedance measurement can for example take $1/64$ seconds. Within a sweep, multiple measurements can be taken at each frequency, for example 12 measurements at each frequency, and a sweep can cover around 16 discrete frequencies ($1/64 \times 12 \times 16 = 3s$). These values are provided simply to give a feeling for the orders of magnitude involved.

In each graph, the top (larger error) dotted line plot shows the uncorrected Cole-Cole function and the bottom (smaller error) solid line plot shows the corrected Cole-Cole function using the method of the invention.

There are other models which can be used, and accurate model parameters can again be obtained more quickly by using the approach of the invention. Examples of other models are the Konturri skin resistance model and Tregear's model of skin resistance.

The bioimpedance device of the invention can also be used by professional healthcare workers to assess fluid levels, with a shorter time to an accurate measurement. For example a median error within 0.5% for a 5 minute measurement can be obtained which in turn allows for a shorter measurement period.

The invention is of interest generally for tissue characterisation based on impedance measurements, and particularly tissue characterisation in the thorax area, where there is significant movement caused by breathing. The invention is not limited to a use for detecting fluid build up in the lungs.

The method of the invention provides an improved tissue characterisation model. This is of intermediate diagnostic relevance, since the tissue parameters then need to be derived by mapping the impedance measurements to the improved model, and the parameters then need to be analysed to reach any diagnosis.

The reading arrangement (voltage meter) used to implement the invention is in one example able to measure the phase of the voltage signal (relative to the current signal applied) and thus can have as an input the current signal. Alternatively, this phase information can be derived by the processor (µP1 in FIG. 3).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be storeddistributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A tissue parameters measurement system for detecting fluid build-up in lungs of a user comprising:
   a bioimpedance measurement system comprising:
      a current source configured to apply an AC current to electrodes configured for disposition on the body tissue of the user;
      a controller configured to sweep a frequency $\omega$ of the AC current applied to the body tissue over a plurality of frequencies;
      a volt meter configured to read voltages from the body tissue, at each of the plurality of frequencies repeatedly over a respiratory cycle of the user;
   a breathing monitor configured to monitor or derive a breathing signal B(t) as a function of time t representing the respiratory cycle of the user; and
   a processor configured to:
      receive values of the voltages read a plurality of times at each of the plurality of frequencies, the values being read at a plurality of different respiratory phase over each of the plurality of respiratory cycles of the user,
      calculate a time varying artifacted impedance signal from the values for each of the frequencies,
      receive a tissue characterization function which maps the artifacted impedance signal to tissue parameters,
      modeling a breathing factor function including a term $k(\omega) \cdot B(t)$ for each frequency $\omega$ that models breathing artifacts over the plurality of phases of the user's respiratory cycle wherein $k(\omega)$ is a frequency-dependent parameter of the breathing factor function,
      combining the tissue characterization function with the breathing factor function to generate a breathing corrected tissue characterization function such that values read at the plurality of different phases of the respiratory cycle contribute to the breathing corrected tissue characterization function, and
      extracting tissue parameters indicative of fluid buildup in the lungs from the breathing corrected tissue characterization function.

2. The system as claimed in claim 1, wherein the breathing monitor comprises a belt.

3. The system as claimed in claim 1, wherein the processor is further configured to map the derived frequency-dependent impedance function to the corrected tissue characterization function to derive tissue parameters indicative of fluid build-up in the lungs.

4. The system as claimed in claim 1, wherein the breathing monitor comprises the processor, wherein the processor is further configured to analyze the frequency-dependent impedance function to extract the respiratory cycle.

5. The system as claimed in claim 4, wherein the processor is further configured to derive the respiratory cycle for the plurality of frequencies based on instantaneous impedance signals at each frequency over the plurality of respiratory cycles and an average of the instantaneous impedance signals at each frequency.

6. The system of claim 1, wherein a breathing signal is synchronized with the time varying artifacted impedance signal.

7. The system of claim 6, wherein the breathing signal is combined with the artifacted impedance signal as a normalized multiplicative factor.

8. A tissue parameters measurement method comprising:
applying an AC current to a user's body tissue via a plurality of electrodes electrically connected to a current source;
reading a voltage with a voltmeter from the body tissue at a plurality of different points over each of a plurality of respiratory cycles of the user;
varying the frequency ω of the AC current applied to the body tissue;
with a processor, deriving a breathing artifacted frequency-dependent impedance function from the applied current values and the read voltages at the plurality of different points over the user's respiratory cycle;
monitoring, using a breathing monitor, or deriving, from the frequency-dependent impedance function, a breathing pattern indicative of a respiratory cycle of the user wherein the breathing pattern comprises a breathing factor function which is a function of time and which includes a parameter $k(\omega)$ that depends on the frequency ω of the AC current applied to the body tissue,
with the processor, processing a tissue characterization function, the monitored or derived breathing pattern and the breathing artifacted frequency-dependent impedance function to correct the tissue characterization function to take account of the plurality of different points in the user's respiratory cycle at which the voltages are read and to derive tissue parameters.

9. The method as claimed in claim 8, wherein the frequency-dependent impedance function is motion artifacted and further including reducing the motion artifacted frequency-dependent impedance function during maximum inhalation and increasing the motion artifacted frequency-dependent impedance function during maximum exhalation.

10. A non-transitory computer-readable medium carrying software configured to control a computer to perform the method of claim 8.

11. The method according to claim 8, wherein processing the corrected tissue characterization function further includes mapping the derived frequency-dependent impedance function to the corrected tissue characterization function to derive tissue parameters indicative of fluid build-up in the lungs.

12. The method as claimed in claim 8, wherein monitoring or deriving a breathing pattern comprises using a belt.

13. The method as claimed in claim 12, further comprising mapping the derived frequency-dependent impedance function to the corrected tissue characterization function to derive tissue characterisation parameters.

14. The method as claimed in claim 8, wherein monitoring or deriving a breathing pattern comprises analyzing the frequency-dependent impedance function to extract the respiratory cycle.

15. The method as claimed in claim 14, wherein analyzing the frequency-dependent impedance function comprises deriving the respiratory cycle for a set of frequencies based on an instantaneous impedance signal at each of the frequencies and an average impedance signal at each of the frequencies.

16. A tissue parameters measurement system comprising:
a bioimpedance measurement system configured to in each of a plurality of sweeps, apply an AC current to electrodes configured to be disposed in contact with skin of a user at each of a plurality of frequencies and, in each of the sweeps, repeatedly output a frequency-dependent impedance function which is artifacted by user breathing; and
one or more processors configured to:
repeatedly, in each respiratory cycle of the user over a plurality of respiratory cycles, receive the breathing artifacted frequency dependent impedance function over different points in the respiratory cycles,
receive respiratory cycle information of the user,
temporally synchronize the breathing artifacted frequency-dependent impedance function with the breathing cycle information, and
adjust the motion artifacted frequency-dependent impedance function based on the respiratory cycle information at a corresponding point in the respiratory cycle to generate breathing artifact corrected tissue parameters.

17. The system as claimed in claim 16, wherein adjusting the motion artifacted frequency-dependent impedance function includes reducing the motion artifacted frequency-dependent impedance function during maximum inhalation and increasing the motion artifacted frequency-dependent impedance function during maximum exhalation.

18. The system as claimed in claim 16, the one or more processors is further configured to map a derived frequency-dependent impedance function to the corrected tissue characterization function to derive tissue parameters indicative of fluid build-up in the lungs.

* * * * *